United States Patent
Ashida

(10) Patent No.: US 8,959,745 B2
(45) Date of Patent: Feb. 24, 2015

(54) METHOD OF PRODUCING CUFF OF SPHYGMOMANOMETER HAVING AUTOMATIC CUFF WINDING MECHANISM

(75) Inventor: Tameo Ashida, Takatsuki (JP)

(73) Assignee: Omron Healthcare Co., Ltd., Kyoto (JP)

( * ) Notice: Subject to any disclaimer, the term of this patent is extended or adjusted under 35 U.S.C. 154(b) by 166 days.

(21) Appl. No.: 13/404,225

(22) Filed: Feb. 24, 2012

(65) Prior Publication Data

US 2012/0240377 A1 Sep. 27, 2012

(30) Foreign Application Priority Data

Mar. 24, 2011 (JP) ................................ 2011-066098

(51) Int. Cl.
*B23P 11/00* (2006.01)
*A61B 5/022* (2006.01)

(52) U.S. Cl.
CPC ................................ *A61B 5/02233* (2013.01)
USPC ............................ 29/454; 29/455.1; 600/490

(58) Field of Classification Search
USPC ............ 29/419.1, 449, 451, 454, 455.1, 458; 156/392, 466; 264/308, 310, 312; 493/386, 388, 389
See application file for complete search history.

(56) References Cited

U.S. PATENT DOCUMENTS 5,698,055 A * 12/1997 Benkoczy ...................... 156/149
7,153,270 B2 * 12/2006 Sano et al. .................... 600/499
2005/0182332 A1 8/2005 Sano et al.
2010/0137725 A1 * 6/2010 Takahashi et al. ............ 600/493
2012/0004560 A1 * 1/2012 Sano et al. .................... 600/499

FOREIGN PATENT DOCUMENTS

| JP | 10-314123 A | 12/1998 |
| JP | 2005-230175 A | 9/2005 |
| JP | 2005-237432 A | 9/2005 |
| JP | 2005-305028 A | 11/2005 |
| JP | 2010200893 A * | 9/2010 |

OTHER PUBLICATIONS

Machine Translation of JP 2010-200893 A.*

(Continued)

*Primary Examiner* — Alexander P Taousakis
*Assistant Examiner* — Matthew P Travers
(74) *Attorney, Agent, or Firm* — Osha Liang LLP

(57) ABSTRACT

In a method of producing a cuff of a sphygmomanometer having an automatic cuff winding mechanism, the cuff includes a band-shaped fluid bladder forming a cavity for inserting a user's arm therein, a shape maintenance member wound on the band-shaped fluid bladder, a band-shaped bag wound on the shape maintenance member, and a cylindrical elastic plate housed in the band-shaped bag. The method includes winding the band-shaped fluid bladder on an outer circumferential surface of a cylindrical jig having approximately the same outer diameter as the cavity of the band-shaped fluid bladder, winding the shape maintenance member on an outer circumferential surface of the band-shaped fluid bladder, winding the band-shaped bag on an outer circumferential surface of the shape maintenance member, removing the cylindrical jig from the band-shaped fluid bladder, and housing the cylindrical elastic plate inside the band-shaped bag.

13 Claims, 12 Drawing Sheets

(56) References Cited

OTHER PUBLICATIONS

Patent Abstracts of Japan, Publication No. 10-314123, publication date Dec. 2, 1998 (1 page).
Patent Abstracts of Japan, Publication No. 2005-237432, publication date Sep. 8, 2005 (1 page).
Patent Abstracts of Japan, Publication No. 2005-230175, publication date Sep. 2, 2005 (1 page).
Patent Abstracts of Japan, Publication No. 2005-305028, publication date Nov. 4, 2005 (1 page).
Office Action in counterpart Chinese Patent Application No. 20120085529.9 issued Jan. 20, 2014 (13 pages).

* cited by examiner

METHOD OF PRODUCING CUFF OF SPHYGMOMANOMETER HAVING AUTOMATIC CUFF WINDING MECHANISM

BACKGROUND OF INVENTION

The present invention relates to a method of producing a cuff of a sphygmomanometer having an automatic cuff winding mechanism.

In order to understand the health condition of a patient, it is very important to measure blood pressure information. In recent years, efforts to detect cardiac load or arterial sclerosis have been made by measuring pulse wave, systolic blood pressure, and diastolic blood pressure, the effectiveness of which is widely known as a major indicator to analyze the risks of cardiovascular diseases such as cerebral embolism, cardiac arrest, and cardiac infarction.

A blood pressure information monitoring device is a device to measure these types of blood pressure information and is expected to be further used in the field of early diagnosis, prevention, and treatment. Moreover, blood pressure information includes various kinds of cardiovascular type of information such as various kinds of indicators that indicate systolic blood pressure, diastolic blood pressure, average blood pressure, pulse wave, pulse, and the degree of arterial sclerosis.

Generally, a cuff for a blood pressure information monitoring device (hereafter, simply called cuff) is used to measure the blood pressure information. Here, the cuff means a band-shaped or ring-shaped structure that includes a fluid bladder having an inner cavity, and can be worn on a part of a human body, and can be used for measuring the blood pressure information by applying pressure to an artery by expanding the fluid bladder by supplying a fluid such as a gas or a liquid into the inner cavity.

In recent years, sphygmomanometers are commonly equipped with an automatic cuff winding mechanism that automatically winds a cuff on an upper arm. References that disclose a sphygmomanometer equipped with this kind of automatic cuff winding mechanism are, for example, Publication of Japanese Unexamined Patent Application JP-H10-314123, Publication of Japanese Unexamined Patent Application JP-2005-237432, Publication of Japanese Unexamined Patent Application JP-2005-230175 and Publication of Japanese Unexamined Patent Application JP-2005-305028 and the like.

In the sphygmomanometers disclosed in those patent references, a cuff is arranged so as to surround a hollow portion that is provided on the device main body, and the shape of the hollow portion is configured in a substantially cylindrical shape, which is larger than the outer shape of the upper arm in the state prior to the cuff being wound on the upper arm (in other words, when the cuff is not wound by the cuff winding mechanism), and it is configured such that the cuff can be fitted on the upper arm by reducing the diameter in order to fit to the shape of the upper arm by operating the automatic cuff winding mechanism.

In the sphygmomanometers in which the above configuration is adopted, because winding strength of the cuff is maintained at a certain level on the upper arm for each measurement, stable measuring accuracy can be realized. Also, because a complicated cuff winding operation becomes unnecessary, it can improve convenience.

SUMMARY OF INVENTION

Normally, a band-shaped air bladder, which is housed in a cuff is formed of a relatively soft type sheet-shaped member made of a resin or the like. This air bladder has a characteristic that its surface easily wrinkles in a state when the cuff is wound on a human body because the air bladder is configured by a relatively soft sheet member as described above.

When wrinkles occur in the air bladder, the skin gets wound in the occurring wrinkle and causes blood congestion. The wrinkle adversely affects the measurement accuracy of the blood pressure information when rapid internal pressure fluctuation occurs when the wrinkle disappears or decreases when the air bladder is compressed or decompressed. Moreover, when deep wrinkles occur in the air bladder, an applied area cannot be evenly pressurized or the wrinkle blocks the flow of air to the inner part of the air bladder and an artery cannot be sufficiently pressurized. In addition, because the applied area where the cuff is applied has individual differences, the frequency in the occurrence of wrinkles is different due to differences in shape of the applied area (mainly the differences of perimeter, differences of curvature, and the like), and the occurrence of wrinkles can be a cause to variations in measurement accuracy.

The cuff of sphygmomanometer having above-mentioned automatic cuff winding mechanism is no exception. Suppressing the occurrence of wrinkles as much as possible that occur in the compression working surface in the applied area of the air bladder housed in the cuff (in other words, the inner circumferential surface of the air bladder that is arranged in a ring shape so that the hollow portion is surrounded) is critical.

Accordingly, one or more embodiments of the present invention provide a blood pressure information monitoring device that can measure blood pressure information with high accuracy without causing discomfort to a patient by providing a method for manufacturing a cuff for a blood pressure information monitoring device in which wrinkles are difficult to occur on a compression working surface of a fluid bladder at the time of measuring.

The inventors discovered that, at the time of manufacturing a cuff for a conventional blood pressure information monitoring device, a plurality of members (such as the fluid bladder, a curved elastic plate that winds and fixes a fluid bladder, and a variety of sheet-shaped members that are arranged between these members) are arranged in a generally flat layers state and then are wound to form a ring shaped cult and that this step is causing the wrinkles of the cuff Based on this finding inventors reached the embodiments of present invention.

In other words, according to the conventional manufacturing method, the aforementioned plurality of members is arranged in flat layers. When both ends of these members layered in flat state are curved upward to form a ring structure of the cuff due to the thickness of the layered members, the layers are subjected to significantly different stresses depending on the locations in the layers, i.e. outer surface, inner surface, edge or central position etc. of the layers. The different stresses received by the layers cause excess areas, which are unevenly distributed on a compression working surface of the fluid bladder. As a result, waves are formed on the compression working surface. This is the cause of deep wrinkles occurring when the fluid bladder is being expanded. By improving the manufacturing method of the cat it is possible to significantly suppress the occurrence of wrinkles on the fluid bladder.

One or more embodiments of the present invention include a method of producing a cuff of a sphygmomanometer having an automatic cuff winding mechanism, wherein the cuff comprises a band-shaped fluid bladder forming a cavity for inserting a user's arm therein, a shape maintenance member wound on the band-shaped fluid bladder, a band-shaped bag wound on the shape maintenance member, and a cylindrical elastic plate housed in the band-shaped bag. The method comprises: winding the band-shaped fluid bladder on an outer circumferential surface of a cylindrical jig having approximately the same outer diameter as the cavity of the band-shaped fluid bladder such that an inner circumferential surface of the band-shaped fluid bladder follows the outer circumferential surface of the cylindrical jig; winding the shape maintenance member on an outer circumferential surface of the band-shaped fluid bladder; winding the band-shaped bag on an outer circumferential surface of the shape maintenance member, removing the cylindrical jig from the band-shaped fluid bladder; and housing the cylindrical elastic plate inside the band-shaped bag.

According to one or more embodiments of the present invention, the outer circumferential surface of the band-shaped fluid bladder and an inner circumferential surface of the shape maintenance member are partially bonded with a double sided tape.

According to one or more embodiments of the present invention, the outer circumferential surface of the shape maintenance member and an inner circumferential surface of the band-shaped bag are partially bonded with a double sided tape.

According to one or more embodiments of the present invention, both lateral side ends of the band-shaped fluid bladder that is wound on the outer circumferential surface of the cylindrical jig are separated by a predetermined distance.

One or more embodiments of the present invention include a method of producing a sphygmomanometer having an automatic cuff winding mechanism, wherein the sphygmomanometer comprises a main body, a substantially cylindrical shell for inserting a user's arm that is rotatably connected to the main body, and a cuff that is housed in the cylindrical shell. The method comprises: winding a band-shaped fluid bladder on an outer circumferential surface of a cylindrical jig having approximately the same outer diameter as the cavity of the band-shaped fluid bladder such that an inner circumferential surface of the band-shaped fluid bladder follows the outer circumferential surface of the cylindrical jig winding a shape maintenance member on an outer circumferential surface of the band-shaped fluid bladder, winding a band-shaped bag on an outer circumferential surface of the shape maintenance member that is wound on the outer circumferential surface of the fluid body; removing the cylindrical jig from the band-shaped fluid bladder; housing the cylindrical elastic plate inside the band-shaped bag; and housing the cuff within the substantially cylindrical shell, wherein the cuff is manufactured by the steps of winding the band-shaped fluid bladder, winding the shape maintenance member, winding the band-shaped bag, removing the cylindrical jig and housing the cylindrical elastic plate.

An advantage of one or more embodiments of the present invention is that due to the use of cylindrical jig wrinkles are difficult to be created on a surface of the fluid bladder, and as such, the blood pressure of the patient can be measured with high accuracy without causing discomfort to the patient at the time of measuring blood pressure.

DETAILED DESCRIPTION OF INVENTION

Figure 1:
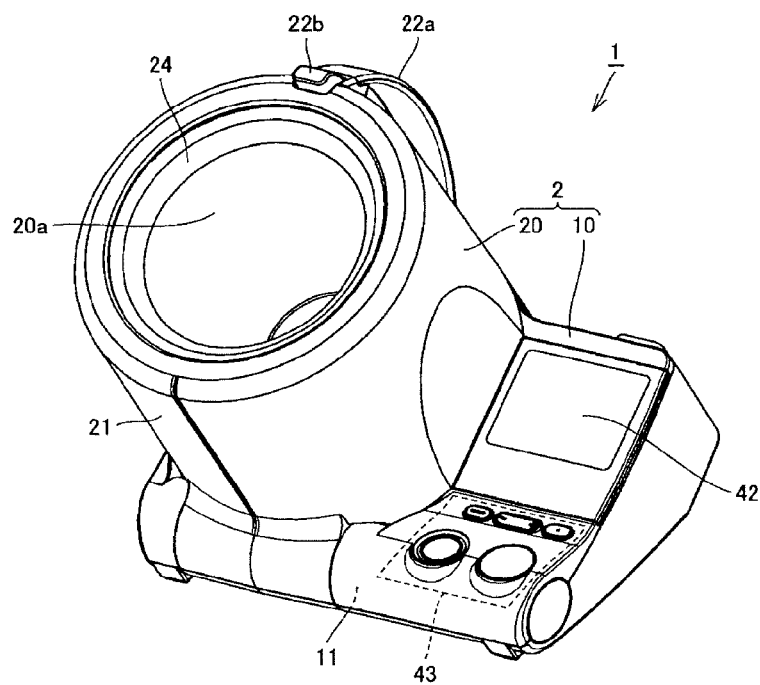
FIG. 1 is a schematic perspective view illustrating a sphygmomanometer equipped with a cuff that is manufactured according to an embodiment of the present invention.
Figure 2:
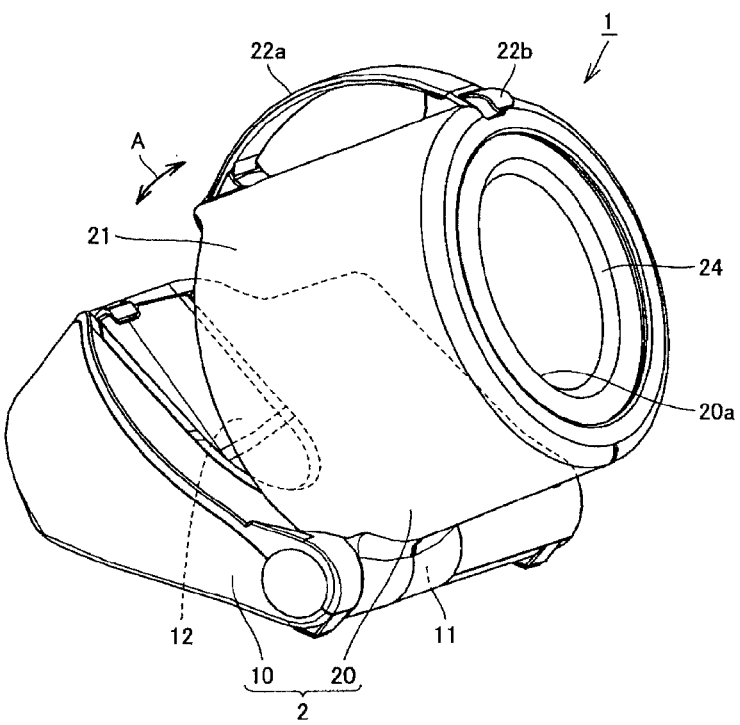
FIG. 2 is a schematic perspective view of when the sphygmomanometer illustrated in FIG. 1 is seen from a different direction.

Hereafter, embodiments of the present invention are explained with reference to drawings. Note that in the embodiments illustrated below, a description is given illustrating an example of a cuff for an upper arm type sphygmomanometer that equips an automatic cuff winding mechanism for the cuff for a blood pressure information monitoring device that is manufactured by one or more embodiments of the present invention FIGS. 1 and 2 are schematic perspective views illustrating a sphygmomanometer having a cuff that is manufactured according to the method of an embodiment of the invention FIG. 1 is a drawing when viewing the sphygmomanometer from the front right oblique upward direction. FIG. 2 is a figure when the sphygmomanometer is viewed from front left oblique upward direction. Note that FIG. 1 illustrates the sphygmomanometer in a state of non-use, and FIG. 2 illustrates the state after an upper arm insertion part is rotated to the position where the upper arm can be inserted. First, a description is provided with reference to FIGS. 1 and 2 of an external structure of the sphygmomanometer equipped with a cuff that is manufactured according to the method for manufacturing the cuff for a sphygmomanometer according to the present embodiment As illustrated in FIG. 1 and FIG. 2, the sphygmomanometer 1 is provided with a device main body 2. The device main body 2 has a main body 10 that includes a mounted surface 11 that is mounted on a mounting surface 200 (refer to FIGS. 6 and 7) such as a table, and an upper aim insertion part 20 that includes a substantially cylindrical hollow part 20a in which the upper arm is inserted.

The main body 10 has a box shaped outer shell, and the above-mentioned mounted surface 11 is configured on the bottom surface thereof and a display part 42 and an operation part 43 are provided in a predetermined position of the upper surface thereof. Inside of the main body 10, a control part 40, to be described below, and a variety of air related components 50 and 60 and the like (see FIG. 5) are mainly housed. Moreover, at the predetermined position of the upper surface of the main body 10 that is adjacent to the display part 42 and the operation part 43, an elbow rest 12 is provided for mounting an elbow when the test patient takes a measuring posture (see FIG. 7). This elbow rest 12 is formed, for example, by providing a recessed part on the upper surface of the main body 10.

The upper arm insertion part 20 has a substantially cylindrical outer shell made of an inelastic shell 21 and high elasticity inner fabric 24, and the above described hollow part 20 is configured by the top surface of the inner fabric 24 that defines the inner circumference surface thereof and a handle part 22a is provided in a predetermined position of the shell 21 that defines the outer circumference surface thereof. This handle part 22a is provided so that the test patient can easily rotate the upper arm insertion part 20 by gripping the handle part 22a, and near the handle part 22a, an unlock button 22b is provided that enables to unlock the upper arm insertion part 20 that is locked by the main body 10 in the non-use state. Moreover, the cuff described below is mainly housed inside of the upper aim insertion part 20.

The upper arm insertion part 20 is connected to the main body 10 with the ability to pivot via a pivot connecting mechanism that is made of, for example, a hinge or the like. More specifically, the upper arm insertion part 20 is configured so as to pivot along the arrow A direction illustrated in FIG. 2 by connecting the position near the front-end part of the main body 10 and the position near the lower end part of the upper arm insertion part 20 with the ability to pivot via the hinge. Accordingly, the upper aim insertion part 20 can be housed compactly by being positioned on the main body 10 when in a non-use state, and it tilts towards the front during use (in other words, towards the test patient side), and it becomes possible to insert the upper aim into the hollow portion 20a.

Figure 3:
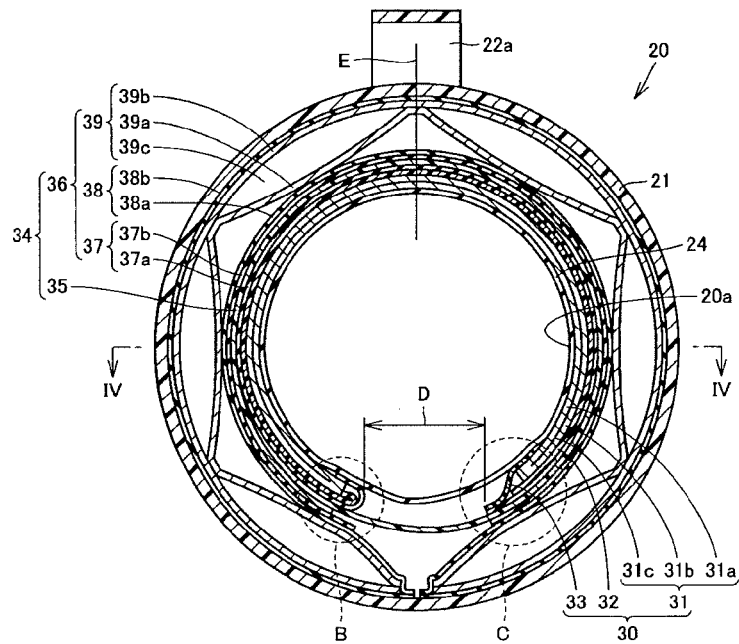
FIG. 3 is a schematic vertical cross-sectional view of the upper arm insertion part of the sphygmomanometer illustrated in FIGS. 1 and 2.
Figure 4:
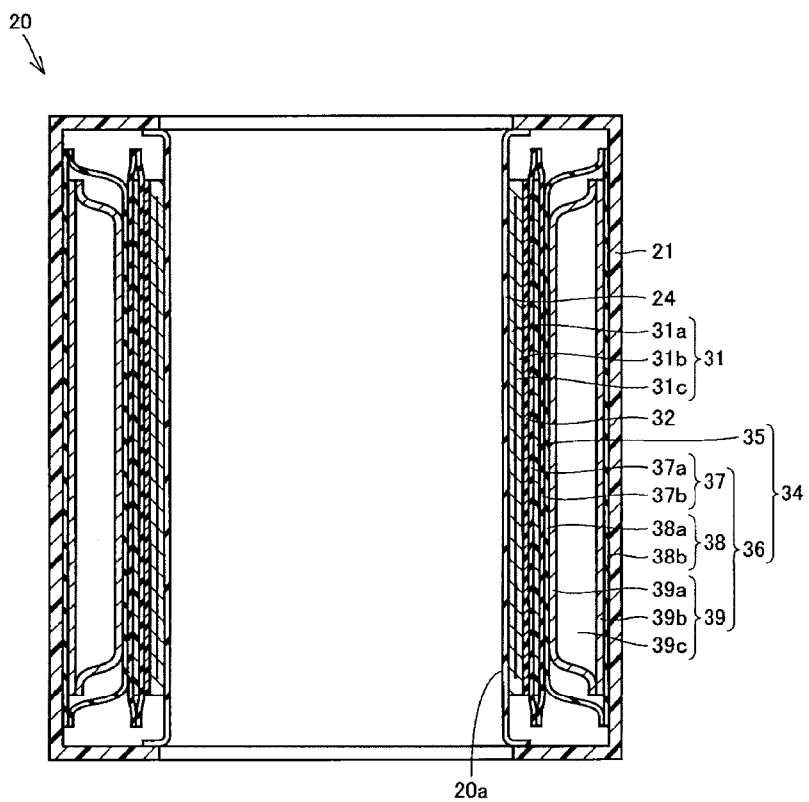
FIG. 4 is a schematic transverse cross-sectional view of the upper arm insertion part of the sphygmomanometer illustrated in FIGS. 1 and 2.

FIGS. 3 and 4 are cross-sectional views of the upper arm insertion part of the sphygmomanometer illustrated in FIGS. 1 and 2. FIG. 3 is a schematic vertical cross-sectional view of when the upper arm insertion part is cut along a plane that is orthogonal to an axis line of the hollow portion. FIG. 4 is a transverse cross-sectional view of when the upper arm insertion part is cut along the line IV-IV illustrated in FIG. 3. Next, a description of an inner configuration of the upper arm insertion part of the sphygmomanometer illustrated in FIGS. 1 and 2 is given with reference to FIGS. 3 and 4.

As illustrated in FIGS. 3 and 4, the upper arm insertion part 20 is provided with a cuff that is configured with an upper arm compression unit 30 and a winding unit 34 in addition to the above described shell 21 and inner fabric 24. The upper arm compression unit 30 includes an upper arm compression air bladder 31 as the fluid bladder, a resin plate 32 as a shape maintenance member, and a slide plate 33. The winding unit 34 includes a curler 35 as a curved elastic plate, a winding air bladder 39 as the fluid bladder for winding, and the first and the second housing bags 37 and 38 as bag bodies.

The upper arm compression air bladder 31, the curler 35, and the winding air bladder 39 are housed and arranged inside the outer shell of the upper arm insertion part 20 that is configured by the shell 21 and the inner fabric 24, and layered in the radial direction. Accordingly, any of the upper arm compression air bladder 31, the curler 35, or the winding air bladder 39 are arranged to surround the hollow portion 20a.

The upper arm compression air bladder 31 is arranged on the most inner layer within the space that is configured by the shell 21 and the inner fabric 24, and is provided adjacent to the inner fabric 24. According to one or more embodiments of the present invention, the upper arm compression air bladder 31 has a band shape and is made out of the bag-shaped member that is formed using a resin sheet.

Specifically, the upper arm compression air bladder 31 has an inner sheet member 31a that is positioned on the inner fabric 24 side and the outer sheet member 31b that is positioned on the shell 21 side, and contains an expansion/retraction space 31c therein. The upper arm compression air bladder 31 is formed in a bag-shape by layering the inner sheet member 31a and the outer sheet member 31b and by welding the peripheral edges thereof. Moreover, the expansion/retraction space 31c that is positioned inside the upper arm compression air bladder 31 is connected via a connecting tube to the upper arm compression air component 50 (see FIG. 5) described later.

Any type of material can be used for the resin sheet that configures the upper arm compression air bladder 31, as long as it has good elasticity and does not leak air from the expansion/retraction space 31c after it is welded. From this view point, according to one or more embodiments of the present invention, an ethylene-vinyl acetate copolymer (EVA) resin, a polyvinyl chloride (PVC) resin, a polyurethane (PU) resin, a polyamide (PA) resin or the like, can be used for the resin sheet The curler 35 is arranged in the space positioned outside of the upper aim compression air bladder 31 within the space configured by the shell 21 and the inner fabric 24, and is made of a substantially cylindrical member that can expand and retract by elastically deforming in the radial direction. More specifically, the curler 35 is configured with the flexible member that has a ring shape, and one end part is layered on the other end part in the circumferential direction. The curler 35 energizes the upper aim compression air bladder 31 towards the upper arm side, and according to one or more embodiments of the present invention, is configured with a member made of polypropylene (PP) resin or the like in order to realize sufficient elasticity.

The winding air bladder 39 is arranged on the most outer layer within the space that is configured by the shell 21 and the inner fabric 24, and it is provided adjacent to the shell 21. According to one or more embodiments of the present invention, the winding air bladder 39 has a band shape appearance and is made of a bag-shape member that is formed by using the resin sheet.

Specifically, the winding air bladder 39 has an inside sheet member 39a that is positional on the inner fabric 24 side and an outside sheet member 39b that is positioned on the shell 21 side, and includes an expansion/retraction space 39c therein.

The winding air bladder 39 is formed in a bag-shape by overlaying the inside sheet member 39a and the outside sheet member 39b and by welding the peripheral edges thereof Moreover, the expansion/retraction space 39c that is positioned inside the winding air bladder 39 is connected to the connecting tube via the air type component 60 for winding described later (refer to FIG. 5).

Any type of material can be used for the resin sheet that configures the winding air bladder 39 as long as it has good elasticity and does not leak air from the expansion/retraction space 39c after it is welded. From this perspective, according to one or more embodiments of the present invention, an ethylene-vinyl acetate copolymer (EVA) resin, a polyvinyl chloride (PVC) resin, a polyurethane (PU) resin, a polyamide (PA) resin, or the like can be used for the resin sheet.

The outer circumferential surface of the upper aim compression air bladder 31 is covered by the curved shape resin plate 32. The resin plate 32 is to maintain the shape of the upper aim compression air bladder 31 that has a relatively small rigidity in a curved shape, and is fixed to the upper arm compression air bladder 31. Moreover, the radial direction end part of the upper arm compression air bladder 31 is covered by the slide plate 33. The slide plate 33 is a member so that the other side of the radial direction end part of the upper arm compression air bladder 31 smoothly runs up on one end of the radial direction end part at the time of measuring, and is configured by a relatively hard member.

Moreover, the curler 35 is housed in the first housing bag 37, and the winding air bladder 39 is housed in the second housing bag 38. These first housing bag 37 and second housing bag 38 correspond to low friction members that are to improve the slide of the curler 35, and, for example, fabric or the like can be used for the material. The first housing bag 37 and the second housing bag 38 are layered along fir radial direction and the first housing bag 37 is arranged inside, and the second housing bag 38 is arranged outside. Note that the first housing bag 37 and second housing bag 38 are fixed only at the positions indicated by the symbol E in the drawings.

The first housing bag 37 has an inside fabric member 37a that is positioned at the inner fabric 24 and the outside fabric member 37b that is positioned at the shell 21 side, and includes a first containing room where the curler 35 is housed inside. The second housing bag 38 has an inside fabric member 38a that is positioned at the inner fabric 24 and the outside fabric member 38b that is positioned at the shell 21 side, and contains a second containing room where the winding air bladder 39 is housed.

Accordingly, the inside fabric member 37a of the first housing bag 37 is interposed between the resin plate 32 and the curler 35 so as to cover the outer circumferential surface of the resin plate 32, and the outside fabric member 37b of the first housing bag 37 is interposed between the curler 35 and the winding air bladder 39 so as to cover the outer circumferential surface of the curler 35. Further, the inside fabric member 38a of the second housing bag 38 is interposed so as to cover the inner circumferential surface of the winding air bladder 39.

By configuring as stated above, not only the resin plate 32 and the first housing bag 37 contact so that they are capable of sliding, but also the first housing bag 37 and the curler 35 contact so that they are capable of sliding; therefore, friction resistance that occurs when the resin plate 32 and the curler 35 are arranged so that they directly contact each other can be reduced. Moreover, by configuring in this manner, because the first housing bag 37 and the second housing bag 38 contact so that they are capable of sliding, the friction resistance that occurs when the curler 35 and the winding air bladder 39 are arranged so that they directly contact can be reduced.

As stated above, the upper arm compression unit 30 that includes the upper arm compression air bladder 31 can move smoothly in the circumferential direction along the inner circumferential surface. Moreover, the curler 35 can move smoothly in the circumferential direction along the inner circumferential direction of the winding air bladder 39. Accordingly, when the winding air bladder 39 expands, the diameter of the curler 35 retracts, which allows the upper aim compression air bladder 31 to move along the inner circumferential surface of the curler 35 in accordance with the retraction of the diameter of the curler 35, and therefore, the diameter of the upper aim compression air bladder 31 retracts.

Note that as illustrated in FIG. 3, in the state that the diameter of the curler 35 is not retracted (in other words in the non-wound state), the one end B and the other end C of the circumferential direction of the upper arm compression unit 30 are arranged so that they are mutually spaced, and the space D is provided in the space between the one end B and the other end C. At the one end B of the circumferential direction of the upper arm compression unit 30, the end part of the upper aim compression air bladder 31 is covered by the inside fabric member 37a of the first housing bag 37 being folded, and accordingly, the one end B is configured in a curved shape. Moreover, at the other end C of the circumferential direction of the upper aim compression unit 30, the end part of the upper aim compression air bladder 31 is covered by the slide plate 33, and accordingly, the other end C is configured acutely.

By configuring as stated above, when diameter of the curler 35 retracts, the above mentioned one end B can easily run up on the other end C. Accordingly, as the smooth diameter retraction operation of the upper aim compression unit 30 is realized, the upper aim compression air bladder 31 can move smoothly along the inner circumferential surface of the curler 35.

Figure 5:
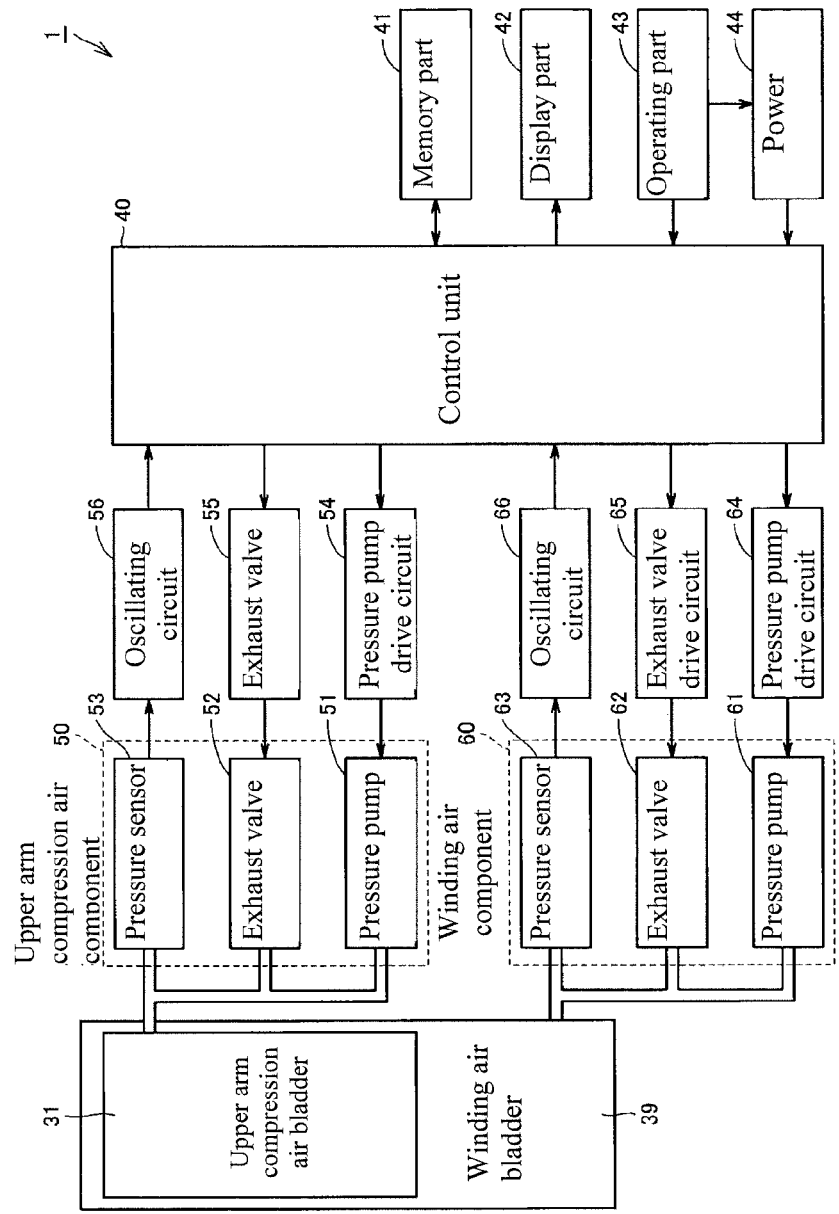
FIG. 5 is a configuration of a function block of the sphygmomanometer illustrated in FIGS. 1 and 2.

FIG. 5 illustrates a function block diagram of the sphygmomanometer illustrated in FIGS. 1 and 2. Next, a description is given with reference to FIG. 5 of the configuration of the function block diagram of the sphygmomanometer illustrated in FIGS. 1 and 2.

As illustrated in FIG. 5, the sphygmomanometer 1, in addition to the above mentioned upper aim compression air bladder 31, the winding air bladder 39, the display part 42, and the operation part 43 are provided with a control unit 40, a memory part 41, a power part 44, an upper aim compression air component 50, and a winding air component 60.

The upper arm compression air component 50 includes a pressure pump 51, exhaust valve 52 and a pressure sensor 53, and the pressure pump 51, exhaust valve 52 and pressure sensor 53 are connected to the above mentioned upper arm compression air bladder 31 via a connecting tube. The pressure pump 51 and the exhaust valve 52 among these correspond to an inflate/deflate mechanism in order to inflate and deflate the upper aim compression air bladder 31. The pressure sensor 53 corresponds to a pressure detecting part that detects the internal pressure of the upper arm compression air bladder 31. Moreover, a pressure pump drive circuit 54, an exhaust valve drive circuit 55, and an oscillation circuit 56 are provided separately in the sphygmomanometer 1 as additional circuitry of the upper arm compression air component 50.

A winding air component 60 includes a pressure pump 61, exhaust valve 62, and a pressure sensor 63, and the pressure pump 61, exhaust valve 62, and a pressure sensor 63 are connected to the above mentioned winding air bladder 39 via a connecting tube. The pressure pump 61 and the exhaust valve 62 among these correspond to an inflate/deflate mechanism in order to inflate and deflate the winding air bladder 39. Moreover, a pressure pump drive circuit 64, an exhaust valve drive circuit 65, and an oscillation circuit 66 are separately provided in the sphygmomanometer 1 as additional circuitry of the winding air component 60.

The control unit 40 is configured by, for example, a central processing unit (CPU) for means to control the entire sphygmomanometer 1. The memory 41 is configured by, for example, Read-Only Memory (ROM) or Random-Access Memory (RAM) for means to store a program to the control unit 40 or the like and to execute processing orders for measuring a blood pressure value and to store the measured results or the like.

The display 42 is configured by, for example, a liquid crystal display (LCD) for means to display the measured results. The control unit 43 is means to receive operation by the test patient or the like and to input this external order into the control unit 40 or the power part 44. The power part 44 is means to supply the power to the control unit 40.

The control unit 40 inputs the control signal into the pressure pump drive circuits 54 and 64 and the exhaust valve drive circuits 55 and 65, respectively, to drive the pressure pumps 51 and 61 and the exhaust valves 52 and 62, and inputs the blood pressure value as the measured result into the memory part 41 or the display part 42. Moreover, the control unit 40 includes the blood pressure information obtaining part (not illustrated) that obtains the blood pressure of the test patient based on the pressure value that is detected by the pressure sensor 53, and the blood pressure that is obtained by this blood pressure obtaining part is input into the above mentioned memory part 41 or the display part 42 as the measured result Moreover, the control unit 40 determines the pressure condition of the winding air bladder 39 based on the pressure value that is detected by the pressure sensor 63.

Moreover, the sphygmomanometer 1 can have a separate output part that outputs the blood pressure value as the measured result to an external device (for example, a personal computer (PC), printer or the like). As the output part, for example, a writing device or the like for a serial communication circuit or various kinds of recording media can be used The pressure pump drive circuit 54 controls the operation of the pressure pump 51 based on the control signal that is input from the control unit 40. The pressure pump 51 increases the pressure within the upper arm compression air bladder 31 (hereafter, refereed to as "cuff pressure"), and its operation is controlled by the above mentioned pressure pump drive circuit 54.

The exhaust valve drive circuit 55 controls the opening and closing operation of the exhaust valve 52 based on the control signal that is input by the control unit 40. The exhaust valve 52 maintains the internal pressure of the upper arm compression air bladder 31 and externally releases the expansion/retraction space 31$c$ of the upper arm compression air bladder 31 in order to reduce pressure, and its operation is controlled by the exhaust valve drive circuit 55.

The pressure sensor 53 is a capacitance type sensor and the capacity changes depending on the internal pressure of the upper arm compression air bladder 31. The oscillating circuit 56 generates a signal of an oscillating frequency according to the capacitance of the pressure sensor 53, and inputs the generated signal into the control unit 40.

The pressure pump drive circuit 64 controls the operation of the pressure pump based on the control signal that is input by the control unit 40. The pressure pump 61 increases the pressure within the winding air bladder 39 by supplying air to the expansion/retraction space 39$c$ of the winding air bladder 39, and its operation is controlled by the above mentioned pressure pump drive circuit 64.

The exhaust valve drive circuit 65 controls the opening and closing operation of the exhaust valve 62 based on the control signal that is input by the control unit 40. The exhaust valve 62 maintains the internal pressure of the winding air bladder 39 and externally releases the expansion/retraction space 39$c$ of the winding air bladder 39 in order to reduce pressure, and its operation is controlled by the exhaust valve chive circuit 65.

The pressure sensor 63 is a capacitance type sensor, and the capacity changes according to the internal pressure of the winding air bladder 39. The oscillating circuit 66 generates a signal of an oscillating frequency according to the capacitance of the pressure sensor 63, and inputs the generated signal into the control part 40.

Figure 6:
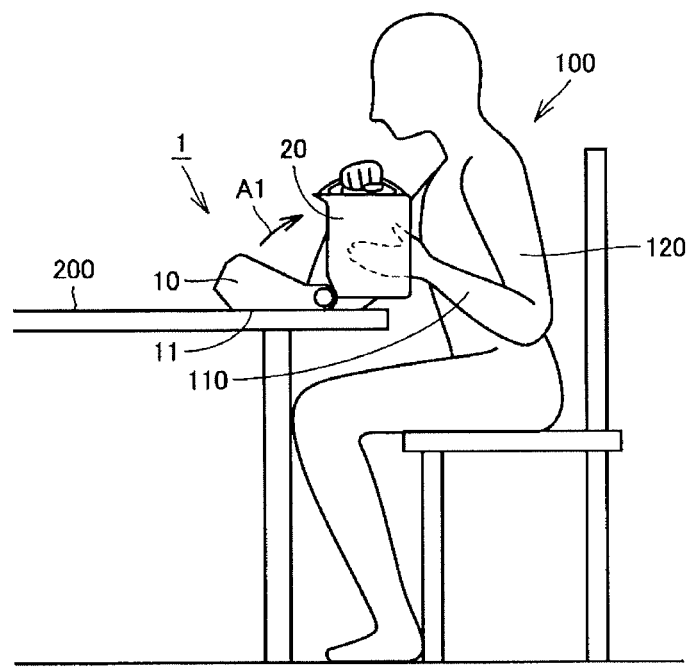
FIG. 6 illustrates a fitting procedure of the sphygmomanometer illustrated in FIGS. 1 and 2 and illustrates a manner in which an arm is inserted into a hollow portion of the upper arm insertion part.
Figure 7:
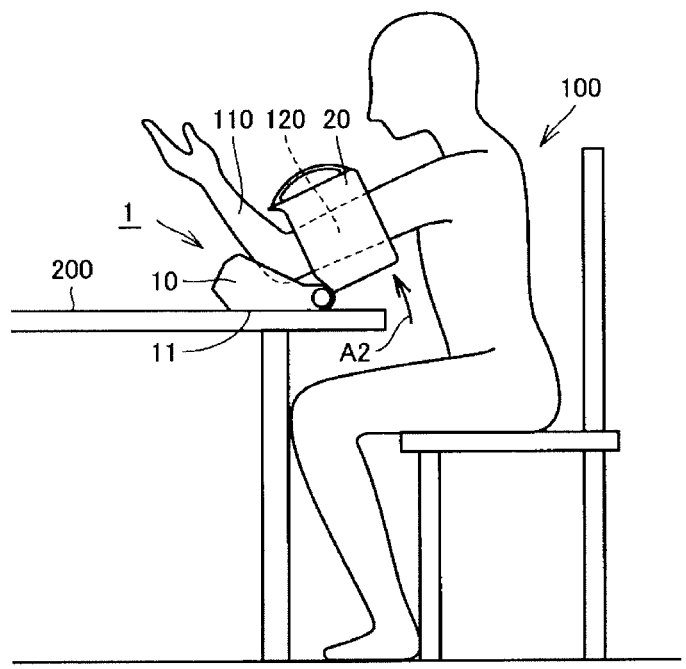
FIG. 7 illustrates a measuring posture when the sphygmomanometer illustrated in FIGS. 1 and 2 is used.

FIG. 6 is a schematic diagram illustrating a fitting procedure of the cuff for the sphygmomanometer illustrated in FIGS. 1 and 2, and illustrates a manner of inserting an arm into a hollow portion of the upper arm insertion part. Moreover, FIG. 7 is a schematic diagram illustrating a measuring posture when the sphygmomanometer is used as illustrated in FIGS. 1 and 2. Moreover, in these FIGS. 6 and 7, a case of when the upper arm of the left arm is used as the measured part is illustrated Next, a description is provided with reference to FIGS. 6 and 7 of the fitting procedure of the cuff and the measuring posture for when the sphygmomanometer illustrated in FIGS. 1 and 2 is used As illustrated in FIG. 6, when the blood pressure value is measured by using the sphygmomanometer 1, the main body 10 of the sphygmomanometer 1 is placed on a table or the like that has a horizontal mounting surface 200, and the test patient 100, for example, is seated in a chair. Further, the test patient holds a handle part 22$a$ that is provided at the upper arm insertion part 20 with the right hand, and presses the unlock button 22$b$, and moves the upper arm insertion part hi the arrow A1 direction in the figure. Further, the test patient inserts the front arm 110 of the left arm into the hollow portion 20$a$ of the upper arm insertion part 20 while adjusting the inclination of the upper arm insertion part 20 with the right hand.

The test patient 100 arranges the upper arm 120 of the left arm inside of the hollow portion 20$a$ by inserting the left arm deeper inside of the hollow portion 20$a$. Then, the test patient 100 takes the measuring position illustrated hi FIG. 7 by slightly bending the elbow of the left arm that is inserted in the hollow portion 20$a$, and placing the elbow on the elbow rest 12 that is provided on the upper surface of the main body 10. Moreover, at this time, the upper arm insertion part 20 rotates to the arrow A2 direction in the figure by following the movement of the left arm until finally stopping at the angle position that corresponds to the inclination of the upper arm 120 of the left arm.

Figure 8:
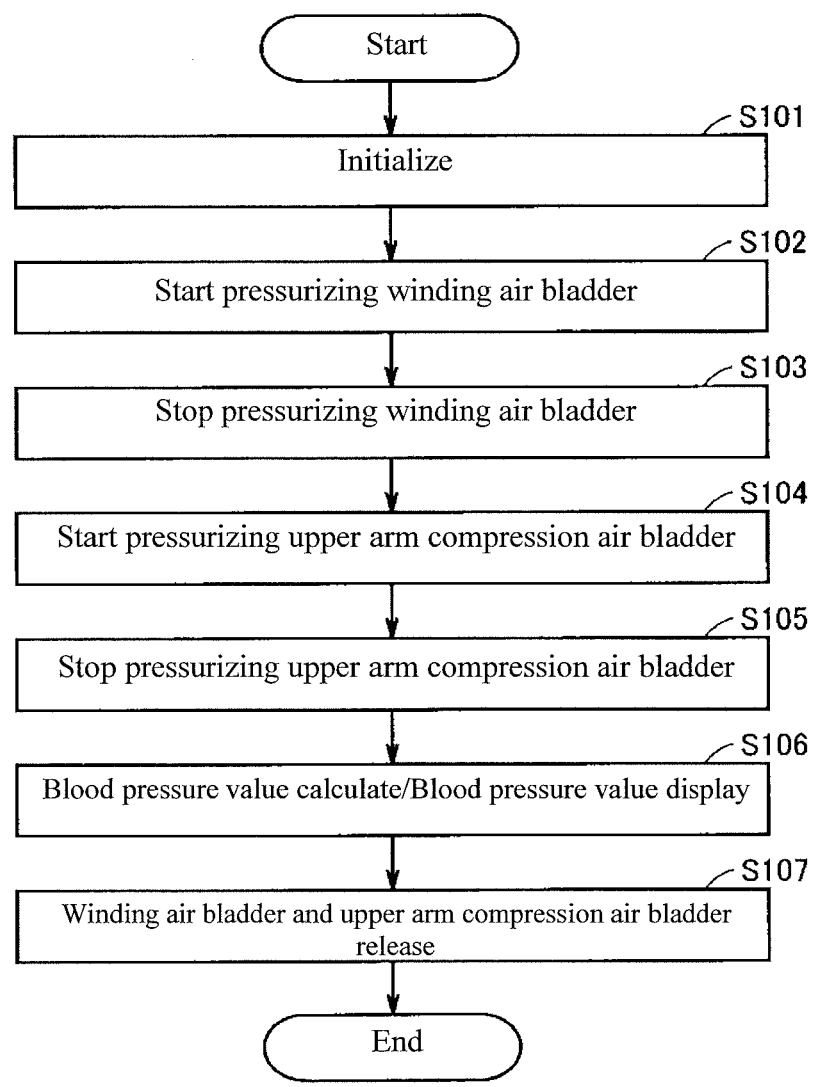
FIG. 8 illustrates an operational flow of the sphygmomanometer illustrated in FIGS. 1 and 2.

FIG. 8 is an operation flow of the sphygmomanometer illustrated in FIGS. 1 and 2. Next, a description of the operation flow of the sphygmomanometer illustrated in FIGS. 1 and 2 is given with reference to FIG. 8. Moreover, the program according to the flow chart is stored in the memory part 41 in advance, and its processing is executed by the control unit 40 to read and execute this program from the memory part 41.

When measuring the blood pressure value, the test patient 100 takes the measuring posture illustrated in the above-mentioned FIG. 7, and turns on the power of the sphygmomanometer 1 by operating the operating part 43 that is provided on the main body 10 in this state. Accordingly, the power is supplied from the power part 44 to the control unit 40, and the control unit 40 drives. As illustrated in FIG. 8, first of all, the control unit 40 initializes the sphygmomanometer 1 (Step S101).

Next, the control unit 40 waits for the order to start measuring by the test patient 100, and when the test patient 100 gives the order to start the measuring by operating the operating part 43, it drives the pressure pump 61 and starts adding pressure to the winding air bladder 39 as well as closes the exhaust valve 62 (Step S102), and raises the pressure until the internal pressure of the winding air bladder 39 becomes a predetermined value. When the internal pressure of the winding air bladder 39 reaches the predetermined value, the driving of the pressure pump is stopped, and the operating part 43 stops adding pressure to the winding air bladder 39 (Step S103). According to one or more embodiments of the present invention, the predetermined value is set to the pressure value in which the winding air bladder 39 is sufficiently expanded and the upper arm compression air bladder 31 is in an allocated state on the upper arm 120, and the control unit 40 may determine whether the pressure value has reached the above mentioned predetermined value based on the signal input by the oscillating circuit 66 to the control unit 40.

Subsequently, the control unit 40 drives the pressure pump 51 and starts adding pressure to the upper aim compression air bladder 31 as well as closing the exhaust valve 52, and gradually increases the cuff pressure (Step S104). In the process of adding pressure to the upper arm compression air bladder 31, the control unit 40 calculates the systolic blood pressure and the diastolic blood pressure using a known procedure. Specifically, the control unit 40 obtains the cuff pressure from the oscillator frequency that is obtained from the oscillating circuit 56 in the process of increasing the cuff pressure of the upper aim compression air bladder 31, and extracts the pulse wave information that is superimposed on the obtained cuff pressure. Then, the control unit 40 calculates the above mentioned blood pressure value based on the extracted pulse wave information.

At Step S104, when the blood pressure value is calculated, the control unit 40 stops adding pressure to the upper arm compression air bladder 31 (Step S105) by stopping the drive of the pressure pump 51. After that, the control unit 40 displays the blood pressure as a measured result on the display part 42 and stores the blood pressure in the memory part 41 (Step S106), and further, the air in the upper arm compression air bladder 31 is completely exhausted by releasing the exhaust valve 52. Also, the air in the winding air bladder 39 is completely exhausted by releasing the exhaust valve 62 (Step S107).

After this, the control unit 40 completes its operation after waiting for the order to trim the power off from the test patient 100. Moreover, the measuring method that is explained above is based on a so-called pressure measuring method that measures the blood pressure by detecting the pulse wave when increasing the cuff pressure at a very slow speed at the time of adding pressure to the upper aim compression air bladder 31. However, it is possible to adopt a so-called decompression measuring method that measures the blood pressure by detecting the pulse wave at the time of when the cuff pressure is decompressed at a very slow speed when the upper arm compression air bladder 31 is being decompressed.

Figure 9:
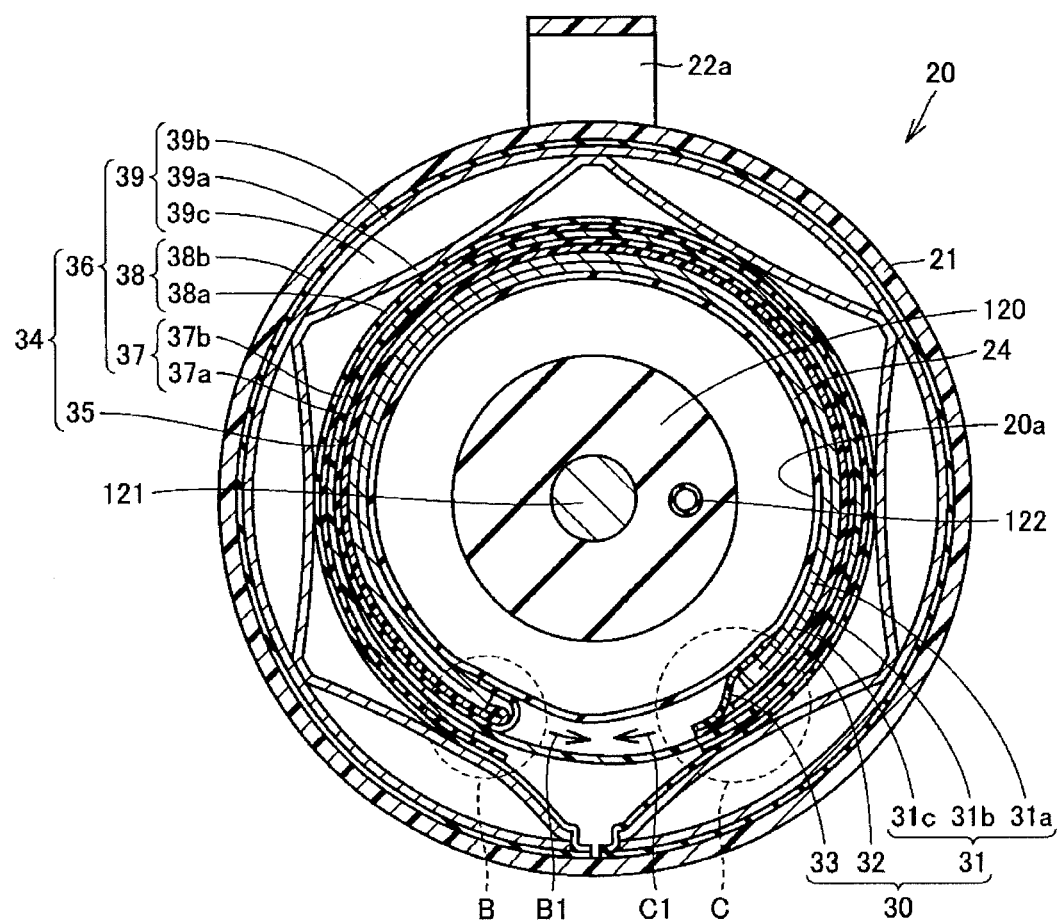
FIG. 9 is a schematic vertical cross-sectional view illustrating a state prior to the winding operation of the cuff of the upper arm insertion part of the sphygmomanometer illustrated in FIGS. 1 and 2.
Figure 10:
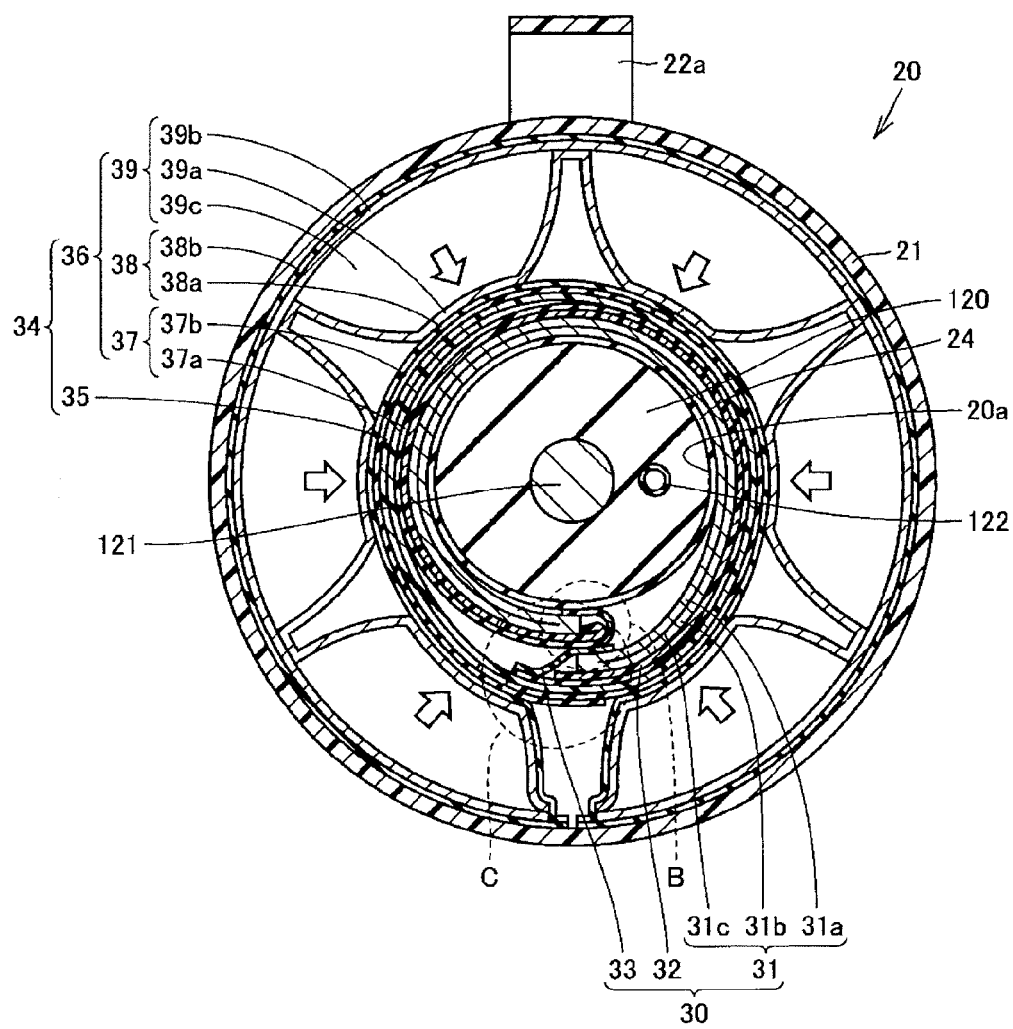
FIG. 10 is a schematic vertical cross-sectional view illustrating a state subsequent to the winding operation of the cuff of the upper arm insertion part of the sphygmomanometer illustrated in FIGS. 1 and 2.

FIG. 9 is a schematic vertical cross-sectional view that illustrates the state prior to the winding operation of the cuff of the upper arm insertion part of the sphygmomanometer illustrated in FIGS. 1 and 2. FIG. 10 is a schematic vertical cross-sectional view that illustrates the state subsequent to the winding operation of the cuff. Moreover, the upper arm 120 that is illustrated in FIGS. 9 and 10 illustrating the upper arm of the left arm, and the cross section illustrated in FIGS. 9 and 10 is a vertical cross section of when the upper arm 120 is seen from the center side to the peripheral side. Next, a description is given with reference to FIGS. 9 and 10 of the winding operation on the upper arm of the upper arm compression unit by the winding unit.

As illustrated in FIG. 9, when the test patient 100 takes the measuring posture illustrated in FIG. 7, the upper arm 120 of the test patient 100 is arranged in the hollow portion 20a of the upper arm insertion part 20. Located inside the upper arm 120 are a humerus 121 and an upper arm artery 122, and when the inserted arm in the hollow portion 20a is the upper arm of the left arm, the upper arm artery 122 is located at the right side part side of the upper arm insertion part 20.

In this state, after the winding operation of the cuff is started, and after adding pressure to the expansion/retraction space 39c of the winding air bladder 39 is started, the winding air bladder 39 starts to expand, and the above mentioned one side end B and the above mentioned other side C of the upper arm compression unit 30 start to move in the direction where both end parts get closer (in other words, the arrow B1 direction and C1 direction illustrated in the drawing) in accordance with the diameter retraction operation of the curler 35. By doing so, the upper arm compression unit 30 starts to retract the diameter.

If the upper arm 120 of the test patient is relatively thick and the perimeter of the upper arm 120 is relatively long, by proceeding with the winding operation of the cuff, the above mentioned one end B and the above mentioned other end C of the upper arm compression unit 30 do not overlap and remain in a state where the space D is present. The inner fabric 24 contacts the upper arm surface on the entire perimeter of the upper arm 120, the upper arm compression air bladder 31 becomes in a wound state around almost the entire perimeter of the upper arm 120, and the winding operation of the cuff is completed.

On the other hand, as illustrated in FIG. 10, when the upper arm of the test patient 120 is relatively thin, and the perimeter of the upper arm 120 is relatively short, by proceeding with the winding operation of the cult the above mentioned one end B and the above mentioned other end C of the upper arm compression unit 30 contact, the above mentioned one end B runs over and overlaps onto the above mentioned other end C, and the inner fabric 24 contacts the entire perimeter of the upper arm surface of the upper arm 120. After this, the upper arm compression air bladder 31 becomes in a wound state around the entire perimeter of the upper arm 120, and the winding operation of the cuff is completed.

By completing the winding operation described above, the upper arm compression unit 30 that includes the upper arm compression air bladder 31 is wound and fixed onto the upper aim 120. In this state, the upper aim 120 of the test patient is effectively compressed by the compression working surface (in other words, the inner circumferential surface of the upper arm compression air bladder 31) of the upper arm compression air bladder 31.

Figure 11:
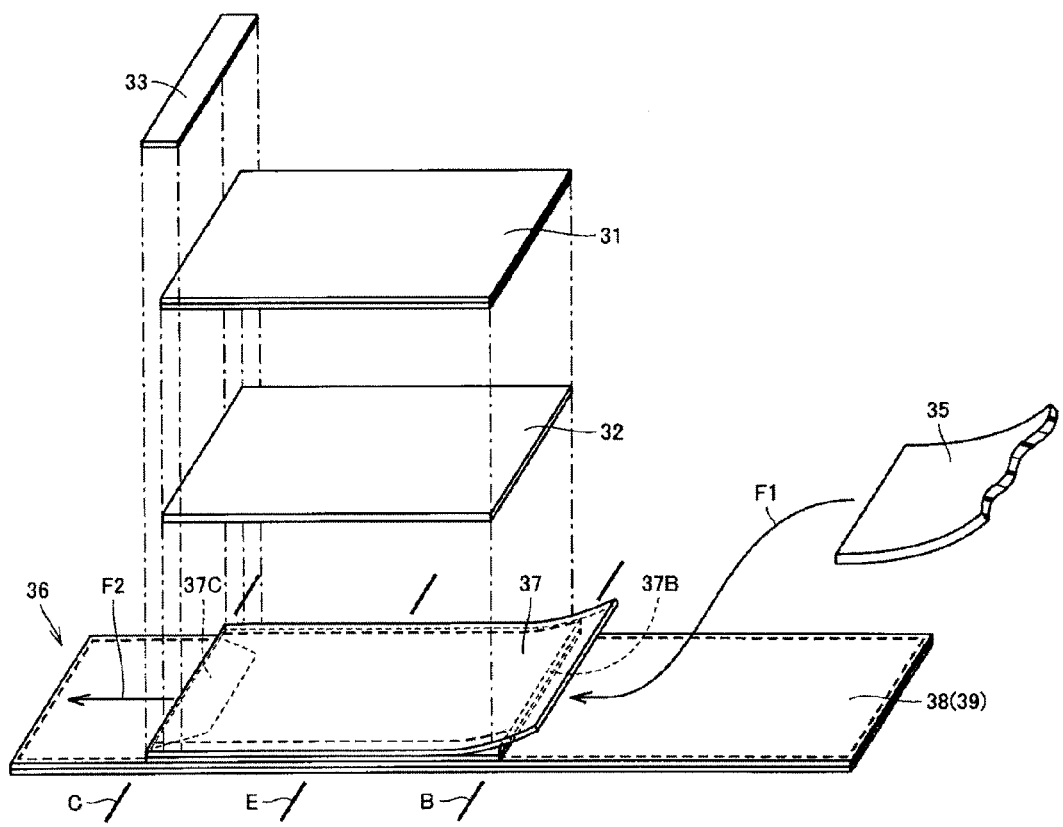
FIG. 11 is an exploded perspective view for an expanded state of the essential parts of the cuff for a sphygmomanometer that is manufactured according to an embodiment of the present invention.

FIG. 11 is an exploded perspective view for an expanded state of the essential parts of the cuff for a sphygmomanometer that is manufactured according to the method for manufacturing the cuff for a sphygmomanometer according to an embodiment of the present invention. Next, a description of the assembly structure is given in further detail with reference to FIG. 11 of the cuff for the sphygmomanometer prior to giving a specific description of the method for manufacturing the cuff for the sphygmomanometer according to an embodiment of the present invention.

As illustrated in FIG. 11, the cuff manufactured according to an embodiment of the present invention is manufactured by assembling the upper arm compression air bladder 31, the resin plate 32, the slide plate 33, a bag-shaped subassembly 36, and the curler 35. The bag-shaped subassembly 36 is already assembled having the first housing bag 37, the second housing bag 38, and the winding air bladder 39.

The second housing bag 38 is formed in a bag-shape by overlaying the long side substantially rectangular shaped inside fabric member 38a and outside fabric member 38b (see FIGS. 3 and 4), and by stitching and/or gluing or the Ike the four sides of the peripheral edges thereof and the winding air bladder 39 is housed therein in advance.

On the other hand, the first housing bag 37 is formed in a bag-like shape in which both end parts 37B and 37C of the lengthwise direction are opened by overlaying the short side substantially rectangular shaped inside fabric member 37a and outside fabric member 37b (see FIGS. 3 and 4), and by stitching and/or gluing or the like the two sides of the peripheral edges thereof (the two sides that are parallel in the lengthwise direction), and the curler 35 is for example, inserted along the F1 direction in the drawing from the one end part 37B so as to be inserted into the inside thereof and pulled out to the F2 arrow direction in the drawing from the other end part 37C. However, according to one or more embodiments of the present invention, the assembly of the curler 35 to the bag body subassembly 36 is performed after the upper arm compression air bladder 31 and the resin plate 32 are assembled onto the bag body subassembly 36 when considering assembling ability at the time of manufacturing the cuff.

The first housing bag 37 and the second housing bag 38 are overlaid in advance, and are fixed only at the positions of the symbol E in the thawing (the position of substantially the center part in the lengthwise direction) by stitching or gluing or the like. Accordingly, the first housing bag 37 and the second housing bag 38 are not fixed at the part as that of the above mentioned both end parts 37B and 37C of the first housing bag 37 (the part that becomes one end B and the other end C of the circumferential direction of the upper arm compression unit 30 after the assembly is completed) or its vicinity.

The resin plate 32, when in a plane view, is made of a sheet shaped member where its external form is approximately the same size as the first housing bag 37, and, for example, is glued and fixed to the inner circumferential surface of the first housing bag 37 by, for example, a bonding member such as double sided tape. Moreover, the external form of the upper arm compression air bladder 31 is approximately the same size as the resin plate 32 when in a plane view, and the inner circumferential surface of the resin plate 32 is glued and fixed by, for example, the double sided tape or the like.

Moreover, the slide plate 33 is glued and fixed on the side where the other end part 37C of the first containing bag 37 is positioned so as to span between the inner circumferential surface of the upper arm compression air bladder 31 and the inner circumferential surface of the first housing bag 37 so as to cover the end part of the upper arm compression air bladder 31.

Note that the assembly stmt.=explained above is only to explain the assembly relationships between each member based on the expanded state of each member for convenience in understanding prior to explaining the actual assembly procedures. The actual assembly procedures are explained in detail below.

Figure 12:
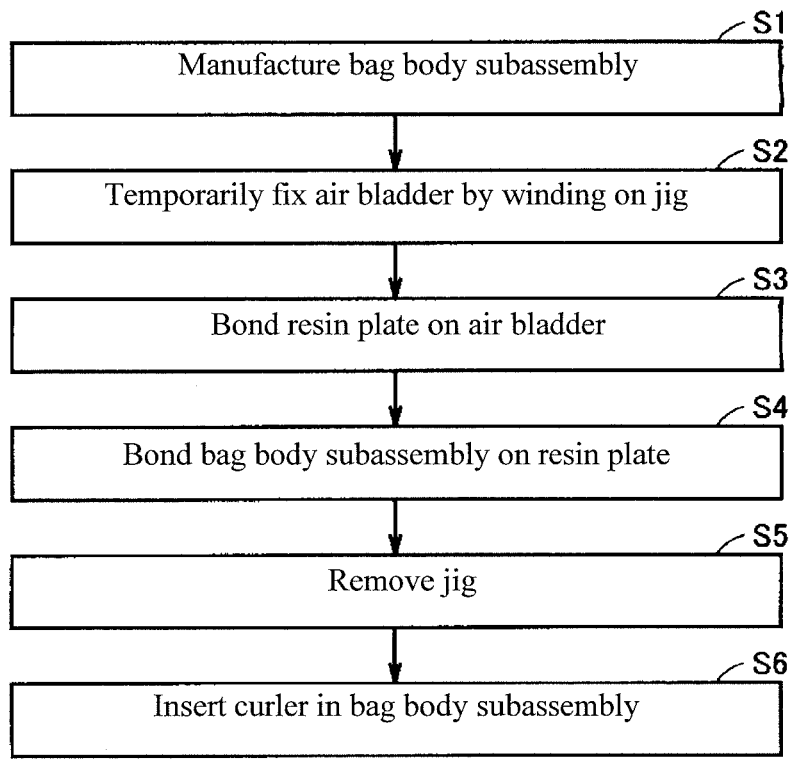
FIG. 12 illustrates a manufacturing flow according to an embodiment of the present invention.

FIG. 12 illustrates a manufacturing flow according to the method of an embodiment of the present invention. FIGS. 13 to 18 are schematic diagrams illustrating a manufacturing process according to the method for manufacturing the cuff for the sphygmomanometer according to one or more embodiments of the present invention. Hereafter, a description is given with reference to FIGS. 12 to 18 of a specific assembly procedure of the method for manufacturing the cuff for the sphygmomanometer according to an embodiment of the present invention.

With the manufacturing method for the cuff for the sphygmomanometer, first of all, as illustrated in FIG. 12, the bag body subassembly 36 is manufactured (Step S1). The bag body subassembly 36, as stated above, the first containing bag 37, the second housing bag 38 and the winding air bladder 39 are manufactured respectively, and manufactured by assembling these in advance.

Figure 13:
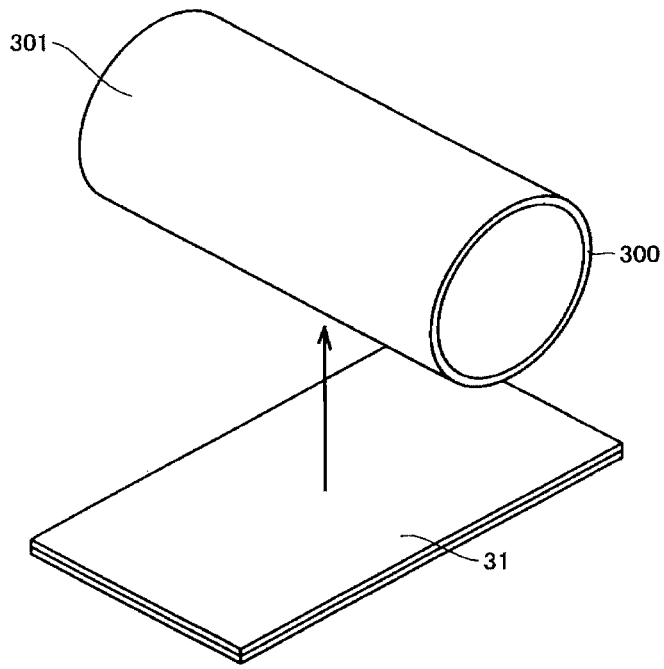
FIG. 13 is a schematic diagram illustrating a manufacturing process according to an embodiment of the present invention.
Figure 14:
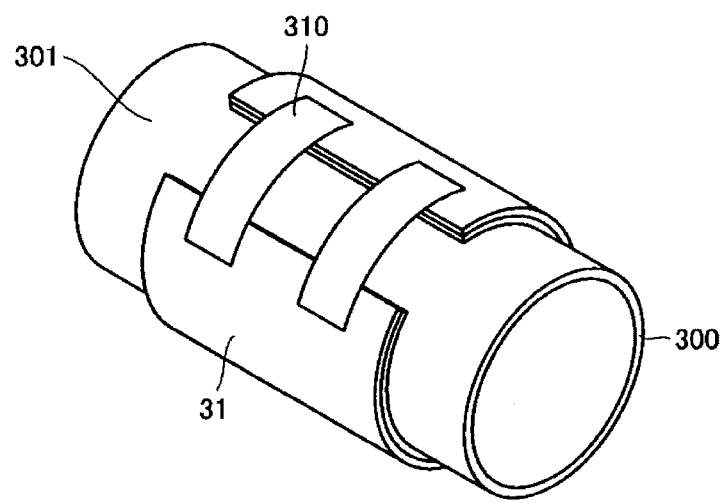
FIG. 14 is a schematic diagram illustrating a manufacturing process according to an embodiment of the present invention.

Next, as illustrated in FIG. 12, the upper arm compression air bladder 31 that is manufactured in advance is wound and temporarily fixed (Step S2) to the jig 300 (see FIGS. 13 and 14). Specifically, as illustrated in FIG. 13, the cylindrical jig 300 having a circumferential surface 301 that is ring shaped and curved is prepared, and the upper aim compression air bladder 31 is arranged by winding so that the inner circumference of the upper aim compression air bladder 31 follows the circumferential surface 301 of the jig 300, and after that, as illustrated in FIG. 14, the upper aim compression air bladder 31 that is wound on the jig 300 is temporarily welded by using the temporary welding tape 310.

Figure 15:
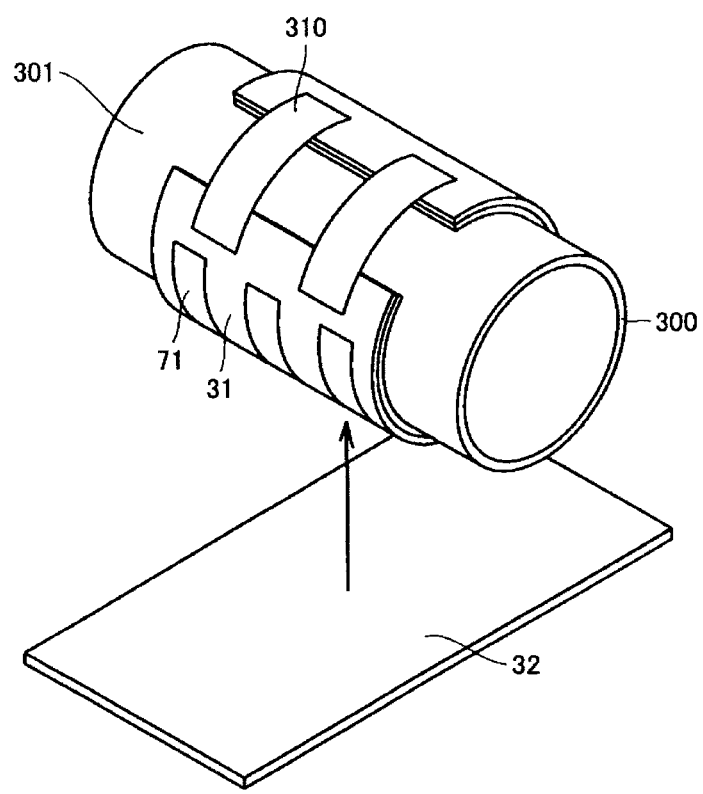
FIG. 15 is a schematic diagram illustrating a manufacturing process according to an embodiment of the present invention.
Figure 16:
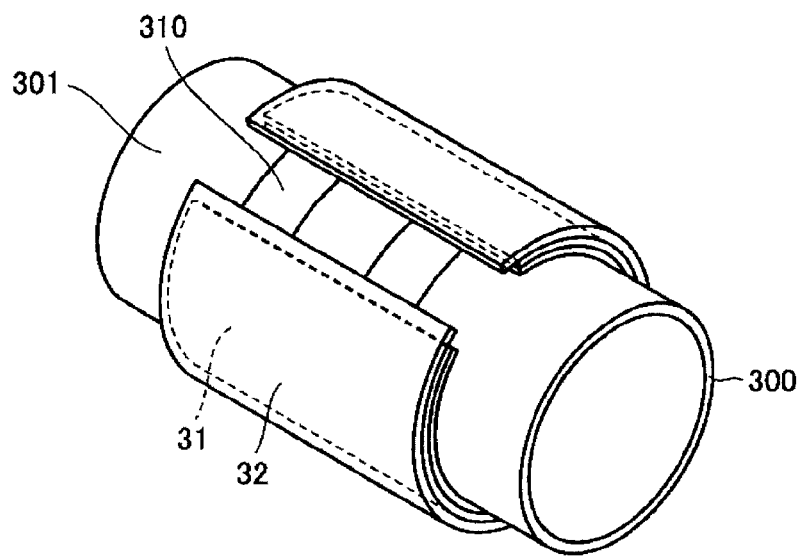
FIG. 16 is a schematic diagram illustrating a manufacturing process according to an embodiment of the present invention.

Next, as illustrated in FIG. 12, the resin plate 32 is glued to the upper arm compression air bladder 31 (Step S3). More specifically, as illustrated in FIG. 15, a bonding member 71 such as double side tape is applied to the outer circumferential surface of the upper arm compression air bladder 31, and the resin plate 32 is wound and set in place on the upper arm compression air bladder 31 so that the inner circumferential surface of the resin plate 32 follows on the outer circumferential surface of the upper arm compression air bladder 31 where the bonding member 71 is applied. By doing this, as illustrated in FIG. 16, the resin plate 32 is bonded and fixed to the upper arm compression air bladder 31.

Figure 17:
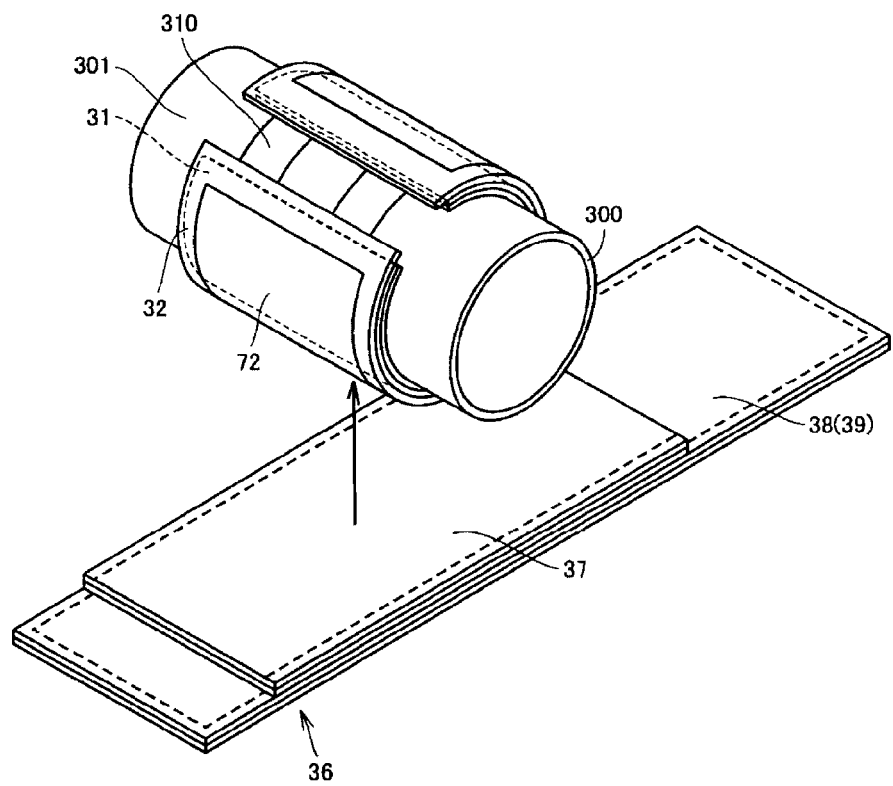
FIG. 17 is a schematic diagram illustrating a manufacturing process according to an embodiment of the present invention.
Figure 18:
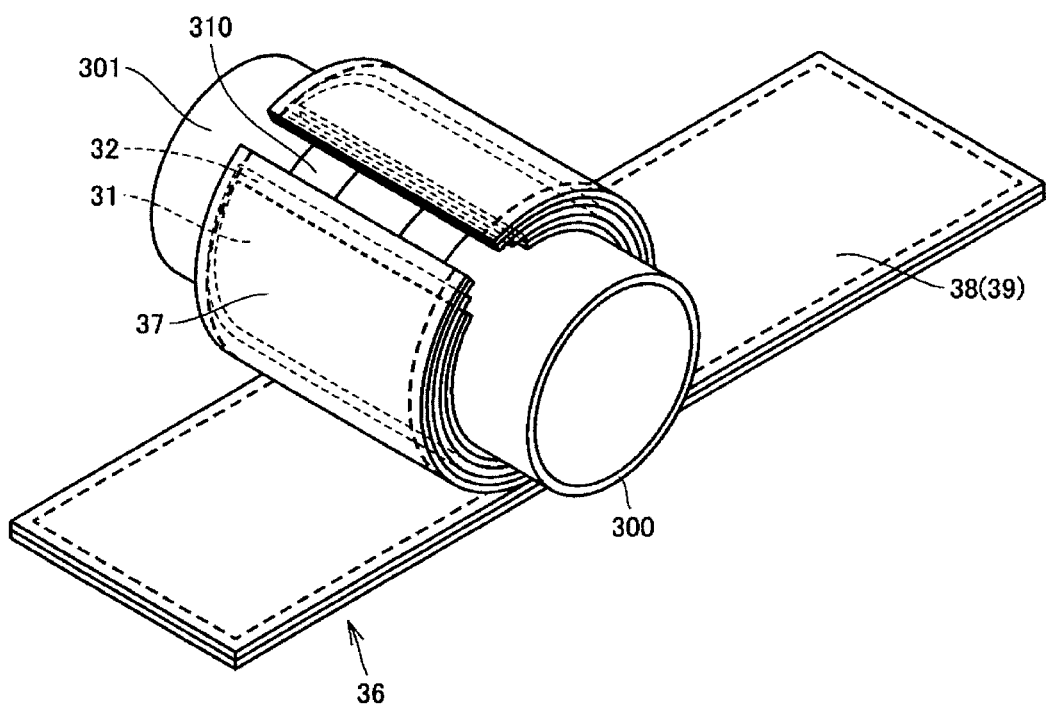
FIG. 18 is a schematic diagram illustrating a manufacturing process according to an embodiment of the present invention.

Next, as illustrated in FIG. 12, the bag body subassembly 36 is bonded on the resin plate 32 (Step S4). More specifically, as illustrated in FIG. 17, a bonding member 72 such as double sided tape is applied to the outer circumferential surface of the resin plate 32 that is set in place on the upper aim compression air bladder 31, and the first housing bag 37 is wound and applied to the resin plate 32 so that the inner circumferential surface of the first housing bag 37 of the bag body subassembly 36 follows on the outer circumferential surface of the resin plate 32 where the bonding member 72 is applied By doing this, as illustrated in FIG. 18, the first housing bag 37 is bonded and fixed to the resin plate 32.

Next, as illustrated in FIG. 12, the jig 300 is removed by removing the temporary welding tape 310 that is applied to the upper arm compression air bladder 31 (Step S5), and after this, the curler 35 is inserted in the first housing bag 37 of the bag body subassembly 36 (Step S6). As stated above, the assembly of the cuff is completed Moreover, assembling the slide plate 33 can be done at any time after the first housing bag 37 is bonded and fixed to the resin plate 32.

By manufacturing the cuff according to the method of an embodiment of the present invention as given above, the upper aim compression air bladder 31, the resin plate 32 that is fixed to the upper arm compression air bladder 31, and the first housing bag 37 of the bag body subassembly 36 that is fixed to the resin plate 32 are each fixed in a curved state in a ring shape. Therefore, in a state where these are mutually fixed and curved in the ring shape, the occurrence of the excess area being unevenly distributed on the compression working surface of the upper arm compression air bladder 31 is prevented.

Accordingly, by assembling the cuff manufactured according to the manufacturing method of one or more embodiments of the present invention onto the upper arm insertion part 20 of the device main body 2 of the sphygmomanometer 1, a state in which waviness hardly occurs on the compression working surface of the upper arm compression air bladder 31 can be realized. Therefore, the degree of wrinkling or frequency of occurrence of wrinkling at the time of expanding the upper arm compression air bladder 31 can be decreased, and the occurrence of wrinkles that occur on the upper arm compression air bladder 31 can be significantly reduced.

By adopting the method for manufacturing the cuff for the sphygmomanometer according to the present embodiment in this manner, because it becomes possible to provide the method for manufacturing the cuff for the sphygmomanometer in which wrinkles are difficult to occur on the compression working surface of the upper arm compression air bladder 31, a sphygmomanometer that can measure blood pressure with high accuracy without giving much discomfort to the test patient can be realized.

Here, as for the above-mentioned jig 300, various kinds of shapes such as a pillar shape or a substantially cylindrical jig that has a notch on one portion may be used other than the cylindrical jig. In other words, any type of shape may be used for the jig 300 as long as the material has a curved circumferential surface with a ring shape.

Moreover, according to one or more embodiments of the present invention, the perimeter of the jig 300 has a size within a range of an applicable perimeter of the upper arm where measurement accuracy is guaranteed when the sphygmomanometer 1 is used For example, when the applicable perimeter of the upper arm is 17 cm-42 cm, according to one or more embodiments of the present invention, a jig 300 with a perimeter range that is 17 cm-42 cm is used. According to one or more embodiments of the present invention, a jig 300 having an external diameter of approximately 5.4 cm-13.4 cm is used.

According to one or more embodiments of the present invention, as for the perimeter of the jig 300, a size in between the maximum applicable perimeter and the minimum applicable perimeter of the upper arm is used where the measurement accuracy is guaranteed when the sphygmomanometer 1 is used. In other words, according to one or more embodiments of the present invention, a jig 300 with a perimeter range that is 29.5 cm is used. According to one or more embodiments of the present invention, a jig 300 having an external diameter of approximately 9.4 cm is used.

By manufacturing the cuff that uses this kind of size of the jig 300, because the upper arm compression air bladder 31 is compressed against the upper arm in a state where the diameter of the curler 35 is retracted and a situation where hardly any wrinkles occur on the compression working surface of the upper arm compression air bladder 31 can be made, the degree of wrinkles that occur and the frequency of wrinkles that occur at the time of expanding the upper arm compression air bladder 31 can be dramatically reduced thereafter.

Although the above description is given in which the method for manufacturing according to one or more embodiments of the present invention is adopted for the cuff equipped to a sphygmomanometer that is provided with the device main body that has a configuration where the main body part includes the mounted surface and the upper arm insertion part includes the hollow portion is connected with the ability to pivot, it is not necessary to separate the device main body into the main body part and the upper arm insertion part, and it is also obviously possible to adopt the method for manufacturing according to one or more embodiments of the present invention for the cuff equipped with a sphygmomanometer that is provided with a single casing that includes the mounted surface and the hollow portion.

Moreover, although a description is given in which the method for manufacturing according to one or more embodiments of the present invention is adopted for the cuff equipped with a sphygmomanometer that is provided with the automatic cuff winding mechanism that is configured so that retracting the diameter of the curler is possible by arranging the winding air bladder as a winding fluid bladder on the outside of the curler that is a curved elastic plate, it is also obviously possible to adopt a method for manufacturing according to one or more embodiments of the present invention for the cuff equipped with a sphygmomanometer that is provided with an automatic cuff winding mechanism that is configured so that the diameter of the curler can be retracted by using some other mechanism.

Furthermore, although a description is given in which the method for manufacturing according to one or more embodiments of the present invention is adopted for the cuff equipped with the upper arm type sphygmomanometer that can measure the blood pressure value of the systolic blood pressure, the diastolic blood pressure or the like, it is also possible to adopt a method for manufacturing according to one or more embodiments of the present invention for the cuff equipped with a wrist-type sphygmomanometer or a foot-type sphygmomanometer. Moreover, it is also obviously possible to adopt the manufacturing method according to one or more embodiments of the present invention not only for a sphygmomanometer that can measure the blood pressure value of systolic blood pressure, the diastolic blood pressure, or the like, but also for a cuff equipped with a blood pressure information monitoring device that can measure the pulse wave, pulse, an index that indicates a degree of arteriosclerosis that represents the Augmentation Index (AI) value, an average blood pressure value, an oxygen saturation degree, or the like.

While the invention has been described with respect to a limited number of embodiments, those skilled in the art, having benefit of this disclosure, will appreciate that other embodiments can be devised which do not depart from the scope of the invention as disclosed herein. Accordingly, the scope of invention should be limited only by the attached claims.

What is claimed is:

1. A method of producing a cuff of a sphygmomanometer comprising an automatic cuff winding mechanism, wherein the cuff comprises a band-shaped fluid bladder foiming a cavity for insetting a user's arm therein, a shape maintenance member wound on the band-shaped fluid bladder, a band-shaped bag wound on the shape maintenance member, and a cylindrical elastic plate housed in the band-shaped bag, the method comprising:

winding the band-shaped fluid bladder on an outer circumferential surface of a cylindrical jig comprising approximately a same outer diameter as the cavity of the band-shaped fluid bladder such that an inner circumferential surface of the band-shaped fluid bladder follows the outer circumferential surface of the cylindrical jig,
  wherein a perimeter of the cylindrical jig has a size within a range of an applicable perimeter of the user's arm;
winding the shape maintenance member on an outer circumferential surface of the band-shaped fluid bladder;

winding the band-shaped bag on an outer circumferential surface of the shape maintenance member;

removing the cylindrical jig from the band-shaped fluid bladder; and housing, after removing the cylindrical jig, the cylindrical elastic plate inside the band-shaped bag.

2. The method of producing the cuff of the sphygmomanometer according to claim 1, wherein the outer circumferential surface of the band-shaped fluid bladder and an inner circumferential surface of the shape maintenance member are partially bonded with a double sided tape.

3. The method of producing the cuff for the sphygmomanometer according to claim 1, wherein the outer circumferential surface of the shape maintenance member and an inner circumferential surface the band-shaped bag are partially bonded with a double sided tape.

4. The method of producing the cuff for the sphygmomanometer according to claim 1, wherein both lateral side ends of the band-shaped fluid bladder that is wound on the outer circumferential surface of the cylindrical jig are separated by a predetermined distance.

5. The method of producing the cuff of the sphygmomanometer according to claim 1, wherein the size of the perimeter of the cylindrical jig within the range of the applicable perimeter of the user's arm is 17 cm-42 cm.

6. The method of producing the cuff of the sphygmomanometer according to claim 1, wherein the size of the perimeter of the cylindrical jig within the range of the applicable perimeter of the user's arm is 29.5 cm.

7. The method of producing the cuff of the sphygmomanometer according to claim 1, wherein the outer diameter of the cylindrical jig is approximately 5.4 cm-13.4 cm.

8. The method of producing the cuff of the sphygmomanometer according to claim 1, wherein the outer diameter of the cylindrical jig is approximately 9.4 cm.

9. A method of producing a sphygmomanometer comprising an automatic cuff winding mechanism, wherein the sphygmomanometer further comprises a main body, a substantially cylindrical shell for inserting a user's arm rotatably connected to the main body, and a cuff housed in the cylindrical shell, the method comprising:

winding a band-shaped fluid bladder on an outer circumferential surface of a cylindrical jig comprising approximately a same outer diameter as a cavity of the band-shaped fluid bladder such that an inner circumferential surface of the band-shaped fluid bladder follows the outer circumferential surface of the cylindrical jig, wherein a perimeter of the cylindrical jig has a size within a range of an applicable perimeter of the user's arm;

winding a shape maintenance member on an outer circumferential surface of the band-shaped fluid bladder;

winding a band-shaped bag on an outer circumferential surface of the shape maintenance member that is wound on the outer circumferential surface of the band-shaped fluid bladder;

removing the cylindrical jig from the band-shaped fluid bladder;

housing, after removing the cylindrical jig, the cylindrical elastic plate inside the band-shaped bag; and housing the cuff within the substantially cylindrical shell, wherein the cuff is manufactured by the steps of winding the band-shaped fluid bladder, winding the shape maintenance member, winding the band-shaped bag, removing the cylindrical jig, and housing the cylindrical elastic plate.

10. The method of producing the sphygmomanometer according to claim 9, wherein the size of the perimeter of the cylindrical jig within the range of the applicable perimeter of the user's arm is 17 cm-42 cm.

11. The method of producing the sphygmomanometer according to claim 9, wherein the size of the perimeter of the cylindrical jig within the range of the applicable perimeter of the user's arm is 29.5 cm.

12. The method of producing the sphygmomanometer according to claim 9, wherein the outer diameter of the cylindrical jig is approximately 5.4 cm-13.4 cm.

13. The method of producing the sphygmomanometer according to claim 9, wherein the outer diameter of the cylindrical jig is approximately 9.4 cm.

* * * * *